United States Patent [19]

Audousset et al.

[11] Patent Number: 5,725,603
[45] Date of Patent: Mar. 10, 1998

[54] PROCESS FOR THE DIRECT DYING OF KERATINOUS FIBRES USING NATURAL DYES AND WATER VAPOR

[75] Inventors: Marie-Pascale Audousset, Asnieres; Jean-Michel Sturla, Saint-Cloud, both of France

[73] Assignee: L'Oreal, Paris, France

[21] Appl. No.: 619,137

[22] Filed: Mar. 20, 1996

Related U.S. Application Data

[63] Continuation of Ser. No. 357,751, Dec. 16, 1994, abandoned.

[30] Foreign Application Priority Data

Dec. 22, 1993 [FR] France ................... 93 15482

[51] Int. Cl.$^6$ .................................................. A61K 7/13
[52] U.S. Cl. .................................. 8/405; 8/646; 8/933
[58] Field of Search ........................... 8/405, 429, 646, 8/933; 132/208

[56] References Cited

U.S. PATENT DOCUMENTS

| | | | |
|---|---|---|---|
| 4,553,339 | 11/1985 | Rigo | 34/99 |
| 5,104,413 | 4/1992 | Ikeda | 8/405 |

FOREIGN PATENT DOCUMENTS

| | | |
|---|---|---|
| 4235436 | 4/1993 | Germany. |
| 61-143315 | 7/1986 | Japan. |

OTHER PUBLICATIONS

English language translation of FR 1,011,151, Amica Co., Jun. 1952, p. 1–14.

*Primary Examiner*—Paul Lieberman
*Assistant Examiner*—Caroline L. Dusheck
*Attorney, Agent, or Firm*—Finnegan, Henderson, Farabow, Garrett & Dunner

[57] ABSTRACT

A process for the direct dyeing of keratinous fibers, which comprises directly dyeing the fibers by contacting the fibers with a composition containing at least one natural dye and with a gas containing water vapor, the temperature of the gas being at least 75° C. and the contact time between the gas and the fibers to be dyed not exceeding two minutes. The hair is dyed uniformly over the whole head of hair, from the roots to the ends, regardless of the condition of the hair.

13 Claims, No Drawings

PROCESS FOR THE DIRECT DYING OF KERATINOUS FIBRES USING NATURAL DYES AND WATER VAPOR

This application is a continuation of application Ser. No. 08/357,751, filed Dec. 16, 1994, now abandoned.

The present invention is directed to a process for the direct dyeing (or colouring) of keratinous fibres, using water vapour and to a composition comprising natural dyes.

The direct dyeing of keratinous fibres, in particular human keratinous fibres such as hair, using natural dyes has been known since ancient times, in particular the use of henna and walnut stain. The use of natural dyes has, for several years, been neglected in favor of the use of synthetic dyes, in particular oxidation dyes. However, direct dyeing is easy to perform and guarantees a good condition of the fibre after dyeing. Moreover, natural dyes are readily available. Natural dyes refer to any dye whose structure exists as it is in nature or whose structure is derived from the hydrolysis or oxidation of a natural precursor product.

There are several reasons why the use of natural dyes is nowadays very limited. On the one hand, natural dyes are very sensitive to the degree of sensitization or the state of degradation of the fibre. In other words, natural dyes are selective. On the other hand, the dyeing power of natural dyes is low even when used with long exposure times. Some natural dyes also have a low light-fastness.

The selectivity of a dye is defined as the difference in uptake, i.e., the difference in dyeing power, of the dye on the hair fibre and depends on whether the hair has to a greater or lesser extent been sensitized or "damaged," either by a treatment such as bleaching or permanent waving or by atmospheric agents, especially in the case of the ends of the hair. Generally speaking, natural dyes are taken up better on slightly sensitized or damaged hair than on natural hair. The dyeing results obtained on hair having differences in sensitization are thus heterogeneous over the whole head of hair. These irregularities are, obviously, not desirable from an aesthetic point of view. The present invention aims to resolve this problem.

It has been found, surprisingly, that the use of a gas comprising water vapour, heated to a temperature of at least 75° C., preferably greater than 75° C., on hair treated with at least one natural dye, enables dyeing results to be obtained which show little dependence on the degree of sensitization of the keratinous fibres being dyed. According to the invention, the hair is dyed uniformly over the whole head of hair, from the roots to the ends, regardless of the condition of the hair. The dyeing is very rapid and the hair has excellent cosmetic properties. In addition, the dyeing displays good light-fastness.

The use of water vapour in a process for oxidation dyeing has been described in French Patent No. 1,011,151, the disclosure of which is incorporated by reference. This French patent teaches the use of water vapour heated to approximately 50° C. to accelerate the process for the oxidation dyeing of hair, while at the same time reducing the amounts of dyes employed. At 50° C., however, there is no decrease in the selectivity problem discussed previously for natural dyes.

The present invention is thus directed to a process for the direct dyeing of keratinous fibres, comprising the step of directly dyeing the fibres, the fibres having previously been contacted with a composition containing at least one natural or direct dye, by contacting the fibres with a gas containing water vapour, the temperature of the gas being at least 75° C., preferably greater than 75° C., and the contact time between the gas and the fibres to be dyed not exceeding two minutes, preferably less than two minutes.

The present invention is also directed to a process for the direct dyeing of keratinous fibres, comprising the step of directly dyeing the fibres by contacting the fibres with a composition containing at least one natural or direct dye and with a gas containing water vapour, the temperature of the gas being at least 75° C., preferably greater than 75° C., and the contact time between the gas and the fibres being sufficient to substantially uniformly dye the fibres.

The present invention also contemplates a process for the direct dyeing of keratinous fibres, comprising the step of directly dyeing the fibres by contacting the fibres with a composition containing at least one natural or direct dye and with a gas containing water vapour, the temperature of the gas and the contact time between the gas and the fibres being sufficient to substantially uniformly dye the fibres.

A further embodiment of the present invention includes a process for the direct dyeing of keratinous fibres, comprising the step of directly dyeing the fibres by contacting the fibres with a composition containing at least one natural or direct dye and with a gas containing water vapour, for a time not exceeding two minutes, preferably less than two minutes, and wherein the gas has a temperature sufficient to substantially uniformly dye the fibres.

A still further embodiment of the present invention includes a process for the direct dyeing of keratinous fibres, comprising the step of directly dyeing the fibres by contacting the fibres with a composition containing at least one natural dye and with a gas containing water vapour, the gas having a temperature of at least 75° C., preferably greater than 75° C., for a contact time between the gas and the fibres to be dyed not exceeding two minutes, preferably less than two minutes.

The process of the present invention is used for the direct dyeing of keratinous fibres in general. The preferred form of keratinous fibres taught by the present invention is human keratinous fibres, such as hair.

The natural dyes can be obtained by synthesis from organisms which produce them or from plants containing them. They may be used either in the form of extracts or in the form of homogenates of all or part of these organisms or plants.

The natural dyes which may be used according to the invention are chosen, for example, from hydroxylated quinones, indigoids, hydroxyflavones, santalins A and B, isatin and its derivatives, and brasilin and its hydroxylated derivative.

The hydroxylated quinones are preferably benzoquinones, naphthoquinones, and mono- or polyhydroxylated anthraquinones which are optionally substituted with groups such as alkyl, alkoxy, alkenyl, chloro, phenyl, hydroxyalkyl and carboxyl.

The naphthoquinones are preferably lawsone, juglone, flaviolin, naphthazarin, naphthopurpurin, lapachol, plumbagin, chloroplumbagin, droserone, shikonin, 2-hydroxy-3-methyl-1,4-naphthoquinone, 3,5-dihydroxy-1,4-naphthoquinone, 2,5-dihydroxy-1,4-naphthoquinone, 2-methoxy-5-hydroxy-1,4-naphthoquinone and 3-methoxy-5-hydroxy-1,4-naphthoquinone.

The benzoquinones are preferably spinulosin, atromentin, aurentioglyocladin, 2,5-dihydroxy-6-methylbenzoquinone, 2-hydroxy-3-methyl-6-methoxybenzoquinone, 2, 5-dihydroxy-3,6-diphenylbenzoquinone, 2,3-dimethyl-5-hydroxy-6-methoxybenzoquinone and 2,5-dihydroxy-6-isopropylbenzoquinone.

The anthraquinones are preferably alizarin, quinizarin, purpurin, carminic acid, chrysophanol, kermesic acid, rhein, aloe emodin, pseudopurpurin, quinizarincarboxylic acid, frangula emodin, 2-methylquinizarin, 1-hydroxyanthraquinone and 2-hydroxyanthraquinone.

The indigoids are preferably indigo, indigoin and Tyrian purple.

The hydroxyflavones are preferably quercetin and morin.

The water vapour may be transported by a carrier gas that may additionally contain solvent vapour. As the vapour, gases such as oxygen and nitrogen, gas mixtures such as air or other vapourizable compounds can be used.

The solvents which may be used for production of the vapour are cosmetically acceptable organic solvents such as alcohols, glycols or glycol ethers. Suitable alcohols include ethanol, isopropanol, benzyl alcohol and phenethyl alcohol. Typical glycol and glycol ethers include monomethyl, monoethyl and monobutyl ethers of ethylene glycol, propylene glycol, butylene glycol and dipropylene glycol, as well as the alkyl ethers such as diethylene glycol monobutyl ether.

The gas preferably comprises at least 1% by volume of water vapour relative to the total volume of the gas. The gas preferably contains either exclusively or essentially water vapour, or consists of a mixture of water vapour and air. The temperature of the gas is at least 75° C., preferably greater than 75° C. The temperature of the gas is more preferably at least 85° C. and even more preferably ranges from 85° C. to 150° C. The temperature of the gas still more preferably ranges from 75° C. to less than 100° C. and most preferably ranges from 85° C. to less than 100° C.

During the process of the present invention, the gas is contacted with the fibres to be dyed for a time period preferably ranging from 0.01 second to 2 minutes, more preferably for a time period ranging from 0.01 second to 30 seconds, and most preferably for a time period ranging from 1 to 10 seconds. Application of the gas may be repeated several times on the same fibres, with each application being conducted for a time period as prescribed above.

In a first embodiment of the present inventive process, which is preferred, a hair dyeing composition containing the natural dyes is applied to the hair, and the hair is subsequently subjected to the action of the water vapour. Another embodiment of the present invention contemplates applying simultaneously the dyeing composition and the gas comprising water vapour to the hair. It is also possible for all or part of the dye composition to be put on the hair by means of the gas flow when some or all of the constituents of the formula can be entrained or vaporized. In another preferred embodiment of the invention, the application of water vapour is followed by rinsing with water.

The production of a hot gas comprising water vapour may be achieved using any apparatus known per se. An apparatus such as that described in French Patent Application No. FR-A-2,273,492, U.S. Pat. No. 4,166,473 or U.S. Pat. No. 4,341,229, the disclosures of which, including the drawings, are incorporated by reference, or any other equivalent apparatus, are preferably used and are particularly suitable.

The dyeing compositions used in the process according to the invention may be provided in forms usually used for dyeing hair, such as a liquid which is thickened or gelled to a greater or lesser extent, a cream, an aerosol foam or any other form suitable for carrying out dyeing of hair. The natural dye content in the dye composition generally ranges from 0.01% to 10% by weight relative to the total weight of the composition.

The compositions used in accordance with the invention are generally aqueous compositions which may contain ingredients usually used in cosmetic compositions intended for dyeing hair, such as solvents, surface-active agents, thickening agents, treating agents, basifying or acidifying agents, preserving agents, fragrances or any other additive used in this type of composition. The dye composition, containing at least one natural dye, has a pH which generally ranges from 2 to 11.

The composition may also be provided in the form of an anhydrous solution or a powder, which forms are diluted at the time of use with water or an aqueous support. The powders thus employed lead to a cataplasm. The anhydrous solutions may be applied directly to wet hair. These supports are, for example, described in French Patent Applications FR-A-2,500,749, FR-A-2,598,318, FR-A-2,526,031 and FR-A-2,500,748, and their English language counterparts, Great Britain Patent No. 2,093,868, U.S. Pat. No. 4,801,302, U.S. Pat. No. 5,259,849 and U.S. Pat. No. 4,602,913, respectively, the disclosures of which are incorporated by reference.

The examples which follow illustrate the invention without limiting the scope of the invention.

In the examples which follow, the support A had the following composition:

| | |
|---|---|
| Behenyltrimethylammonium chloride containing 80% of active material (AM) in a water/isopropanol mixture (15/85) | 0.5 g AM |
| Wood flour | 8 g |
| Hydroxyethyl cellulose | 0.45 g |
| Cetylstearyl ($C_{16}$–$C_{18}$/30–70) alcohol | 8 g |
| Ethylene glycol dicetylstearate ($C_{16}$—$C_{18}$/30–70) | 2 g |
| Oxyethylenated cetytstearyl ($C_{16}$–$C_{18}$//30–70) alcohol with 33 mol of ethylene oxide | 2 g |
| Citric acid qs | pH 4 |
| Water qs | 100 g |

EXAMPLE 1

(Invention)

A dye composition having the following characteristics was used:

| | |
|---|---|
| Support A | 1 g |
| Lawsone | 0.15 g |
| Arlasolve DMI | 4.85 g |
| Water | 5 g |

The above mixture was applied to a lock of natural hair (lock No. 1, $L_1$) and to a lock of this same hair having undergone a permanent wave (lock No. 2, $L_2$). A jet of water vapour at 90° C. was subsequently applied to the two locks for 45 seconds. The locks were rinsed and then dried.

The shades obtained were similar. The selectivity was assessed from a relative value of the differences between the chromatic coordinates L, a and b, which were measured on both of the locks with a MINOLTA CHROMA METER CR 200 colorimeter:

$$\Delta E = \sqrt{[(L_2 - L_1)^2 + (a_2 - a_1)^2 + (b_2 - b_1)^2]}$$

In this example, ΔE was 4.8.

EXAMPLE 2

(Comparative)

The mixture of Example 1 was applied to a lock of natural hair (lock No. 1, $L_1$) and to a lock of this same hair having undergone a permanent wave (lock No. 2, $L_2$). The composition was left to stand for 30 minutes at room temperature. The locks were rinsed and then dried.

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 11.8.

The difference in colouration between the 2 locks, $L_1$ and $L_2$, was very considerable with this process which was not in accordance with the invention. The ΔE, which represents the selectivity, was much higher than in Example 1; however, it should have been as low as possible.

EXAMPLE 3

(Invention)

The process was performed in the same way as in Example 1, with the difference being that the composition used had the following characteristics:

| Support A | 10 g |
|---|---|
| 2,5-Dihydroxy-1,4-naphthoquinone | 0.1 g |
| Arlasolve DMI | 4.9 g |
| Water | 5 g |

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 2.25.

EXAMPLE 4

(Comparative)

The process was performed in the same way as it was in Example 2, using the composition of Example 3.

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 13.9.

The difference in colouration between the locks was very considerable with this process which was not in accordance with the invention. The ΔE, which represents the selectivity, was much higher than in Example 3; however, it should have been as low as possible.

EXAMPLE 5

(Invention)

The process was performed in the same way as in Example 1, with the difference being that the composition used had the following characteristics:

| Support A | 15 g |
|---|---|
| Isatin | 0.1 g |
| Arlasolve DMI | 4.9 g |

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 0.7.

EXAMPLE 6

(Comparative)

The process was performed in the same way as it was in Example 2, using the composition of Example 5.

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 7.3.

The difference in colouration between the 2 locks was considerable with this process which was not in accordance with the invention. The ΔE, which represents the selectivity, was much higher than in Example 5; however, it should have been as low as possible.

EXAMPLE 7

(Invention)

The process was performed in the same way as it was in Example 1, with the difference being that the composition used had the following characteristics:

| Support A | 15 g |
|---|---|
| 2-Hydroxy-3-methyl-1,4-naphthoquinone | 0.1 g |
| Arlasolve DMI | 4.9 g |

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 3.9.

EXAMPLE 8

(Comparative)

The process was performed in the same way as it was in Example 2, using the composition of Example 7.

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, ΔE was 10.3.

The difference in colouration between the 2 locks was very considerable with this process which was not in accordance with the invention. The $\Delta E$, which represents the selectivity, was much higher than in Example 7; however, it should have been as low as possible.

EXAMPLE 9

(Invention)

The process was performed in the same way as it was in Example 1, with the difference that being the composition used had the following characteristics:

| Support A | 15 g |
|---|---|
| 2,5-Dihydroxy-3-methoxy-6-methyl-1,4-benzoquinone | 0.1 g |
| Arlasolve DMI | 4.9 g |

The selectivity was assessed from a relative value of the differences between the chromatic coordinates L, a and b, which were measured on both of the locks with a MINOLTA CHROMAMETER CR 200 colorimeter:

$$\Delta E = \sqrt{[(L_2-L_1)^2+(a_2-a_1)^2+(b_2-b_1)^2]}$$

In this example, $\Delta E$ was 1.7.

The shades were more or less identical.

EXAMPLE 10

(Comparative)

The process was performed in the same way as it was in Example 2, using the composition of Example 9.

The selectivity was assessed from a relative value of the differences between the chromatic coordinates L, a and b, which were measured on both of the locks with a MINOLTA CHROMA METER CR 200 colorimeter:

$$\Delta E = \sqrt{[(L_2-L_1)^2+(a_2-a_1)^2+(b_2-b_1)^2]}$$

In this example, $\Delta E$ was 9.

The difference in colouration between the 2 locks was very considerable with this process which was not in accordance with the invention. The $\Delta E$, which represents the selectivity, was much higher than in Example 9; however, it should have been as low as possible.

What is claimed is:

1. A process for the direct dyeing of keratinous fibres comprising the step of:

directly dyeing said fibres, said fibres having previously been contacted with a composition containing at least one natural dye, by contacting said fibres with a gas containing water vapour, said gas having a temperature of at least 85° C. for a contact time between the gas and the fibres of less than two minutes.

2. A process according to claim 1, wherein the gas has a temperature ranging from 85° C. to 150° C.

3. A process according to claim 1, wherein the gas is contacted with the fibres for a time ranging from 0.01 second to less than 2 minutes.

4. A process according to claim 3, wherein the gas is contacted with the fibres for a time ranging from 0.01 second to 30 seconds.

5. A process according to claim 4, wherein the gas is contacted with the fibres for a time ranging from 1 second to 10 seconds.

6. A process according to claim 1, wherein the contacting of said fibres with said gas is repeated several times on the fibres.

7. A process according to claim 1, wherein the gas exclusively contains water vapour.

8. A process according to claim 1, wherein the gas contains water vapour and at least one other compound in gas or vapour form.

9. A process according to claim 8, wherein the gas contains water vapour and air.

10. A process according to claim 1, wherein said at least one natural dye is a hydroxylated quinone, an indigoid, a hydroxyflavone, santalin A, santalin B, isatin, a derivative of isatin, brasilin, or a hydroxylated derivative of brasilin.

11. A process according to claim 1, wherein said at least one natural dye is present in concentrations ranging from 0.01% to 10% by weight relative to the total weight of the composition.

12. A process according to claim 1, wherein the keratinous fibres are human keratinous fibres.

13. A process according to claim 1, wherein the temperature of the gas ranges from 85° C. to less than 100° C.

* * * * *

UNITED STATES PATENT AND TRADEMARK OFFICE
CERTIFICATE OF CORRECTION

PATENT NO. : 5,725,603
DATED : March 10, 1998
INVENTOR(S) : AUDOUSSET et al.

It is certified that error appears in the above-indentified patent and that said Letters Patent is hereby corrected as shown below:

On the title page, under item [54] and column 1, line 1, "DYING" should read --DYEING--.

In the Abstract, line 2, "75°C" should read --85°C--.

Signed and Sealed this

Fourth Day of August, 1998

Attest:

BRUCE LEHMAN

Attesting Officer

*Commissioner of Patents and Trademarks*